(12) United States Patent
Mo et al.

(10) Patent No.: US 12,394,035 B2
(45) Date of Patent: Aug. 19, 2025

(54) WELD QUALITY INSPECTION METHOD, APPARATUS AND SYSTEM, AND ELECTRONIC DEVICE

(71) Applicant: Guangdong Lyric Robot Automation Co., Ltd., Huizhou (CN)

(72) Inventors: Zhijian Mo, Huizhou (CN); Bing Du, Huizhou (CN); Jiguang Yuan, Huizhou (CN); Yixian Du, Huizhou (CN); Junxiong Zhou, Huizhou (CN); Junjie Zhou, Huizhou (CN)

(73) Assignee: Guangdong Lyric Robot Automation Co., Ltd., Huizhou (CN)

( * ) Notice: Subject to any disclaimer, the term of this patent is extended or adjusted under 35 U.S.C. 154(b) by 383 days.

(21) Appl. No.: 17/917,947

(22) PCT Filed: Apr. 14, 2021

(86) PCT No.: PCT/CN2021/087111
§ 371 (c)(1),
(2) Date: Oct. 10, 2022

(87) PCT Pub. No.: WO2021/213223
PCT Pub. Date: Oct. 28, 2021

(65) Prior Publication Data
US 2023/0139733 A1     May 4, 2023

(30) Foreign Application Priority Data
Apr. 20, 2020 (CN) .......................... 202010313058.7

(51) Int. Cl.
*G06T 7/00*     (2017.01)
*G01N 21/88*     (2006.01)
(Continued)

(52) U.S. Cl.
CPC ....... *G06T 7/0004* (2013.01); *G01N 21/8851* (2013.01); *G01N 33/2045* (2019.01);
(Continued)

(58) Field of Classification Search
CPC .................. G06T 7/0004; G06T 7/12; G06T 2207/10028; G01N 33/207; G01N 33/2045; G01N 21/8851
See application file for complete search history.

(56) References Cited

U.S. PATENT DOCUMENTS

| 10,565,911 B2 | 2/2020 | Li et al. |
| 2013/0304399 A1 | 11/2013 | Chen et al. |
| 2018/0361499 A1 | 12/2018 | Johnson et al. |

FOREIGN PATENT DOCUMENTS

| CN | 101559512 A | * | 10/2009 | |
| CN | 104959719 A | * | 10/2015 | ........... B23K 31/125 |

(Continued)

OTHER PUBLICATIONS

Fan Ling, Welding defect recognition technology based on image processing and machine learning, Ship science and technology, Dec. 2014, vol. 36, No. 12.
(Continued)

*Primary Examiner* — Lisa M Caputo
*Assistant Examiner* — Nyla Gavia
(74) *Attorney, Agent, or Firm* — Daylight Law, P.C.

(57) ABSTRACT

A weld quality inspection method, apparatus and system and an electronic device are disclosed. The weld quality inspection method provided by the embodiments of the disclosure includes: acquiring point cloud data of a target weldment, and converting the point cloud data into a height map; determining a weld region for characterizing a target weld from the height map; analyzing the weld region to obtain a feature parameter of the target weld; and obtaining a quality
(Continued)

inspection result of the target weld according to the feature parameter, where the target weldment includes a base material, a welding part and the target weld formed by welding the welding part to the base material.

10 Claims, 8 Drawing Sheets

(51) Int. Cl.
*G01N 33/2045* (2019.01)
*G01N 33/207* (2019.01)
*G06T 7/12* (2017.01)

(52) U.S. Cl.
CPC ............. *G01N 33/207* (2019.01); *G06T 7/12* (2017.01); *G06T 2207/10028* (2013.01); *G06T 2207/20021* (2013.01); *G06T 2207/30108* (2013.01)

(56) References Cited

FOREIGN PATENT DOCUMENTS

| CN | 105665970 | A | | 6/2016 | |
| --- | --- | --- | --- | --- | --- |
| CN | 107764205 | A | | 3/2018 | |
| CN | 106770394 | B | | 10/2018 | |
| CN | 108776964 | A | | 11/2018 | |
| CN | 109283182 | A | | 1/2019 | |
| CN | 109406173 | A | | 3/2019 | |
| CN | 110047604 | A | | 7/2019 | |
| CN | 110524581 | A | | 12/2019 | |
| CN | 110530877 | A | * | 12/2019 | ......... G01N 21/8806 |
| CN | 210334929 | U | | 4/2020 | |
| CN | 111462110 | B | | 4/2021 | |
| CN | 109752392 | B | | 8/2021 | |

OTHER PUBLICATIONS

International Search Report from Application No. PCT/CN2021/087111, dated Jun. 29, 2021, 4 pages.

M. Malarvel et al., Anisotropic diffusion based denoising on X-radiography images to detect weld defects, Digit. Signal Process. (2017), http://dx.doi.org/10.1016/j.dsp.2017.05.014.

The first office action from Chinese Application No. 2020103130058.7 dated Feb. 26, 2021, 7 pages.

Wang Haixia, Lin Qing, Xu Lin. Weld seam positioning method of container reinforced plate based on structured light. Computer Engineering and Applications, 2011, 47 (23): 220-223.

Written opinion from PCT Application No. PCT/CN2021/087111, dated Jul. 15, 2021, 4 pages.

* cited by examiner ion value.
WELD QUALITY INSPECTION METHOD, APPARATUS AND SYSTEM, AND ELECTRONIC DEVICE

CROSS-REFERENCE TO RELATED APPLICATIONS

This application is a national stage filing under 35 U.S.C. § 371 of international application number PCT/CN2021/087111, filed 14 Apr. 2021, which claims priority to Chinese patent application No. 202010313058.7 filed 20 Apr. 2020. The contents of these applications are incorporated herein by reference in their entirety for all purposes.

TECHNICAL FIELD

The disclosure relates to the technical field of industrial manufacturing, and in particular, to a weld quality inspection method, apparatus and system, and an electronic device.

BACKGROUND

In the technical field of industrial manufacturing, it would typically involve a welding procedure which has high requirements for the precision of a welding tool. In the welding procedure, if the welding tool is low in precision and is inadequately controlled, defects such as unevenness, gas pores, excessive concaves, and burst points may appear on the surface of a weld, which may ultimately affect the quality and the service life of the product. Therefore, before leaving factory, it is usually necessary to inspect the products for weld quality to eliminate products with unqualified weld quality, thereby increasing the product yield. However, at present, most product manufacturers still adopt a manual inspection method to inspect weld quality. This method is influenced by factors such as inspector's proficiency, fatigue and emotion, so the accuracy of an inspection result cannot be guaranteed.

SUMMARY

An object of the embodiments of the disclosure is to provide a weld quality inspection method, apparatus and system, and an electronic device, so as to solve the above problems.

In the first aspect, embodiments of the disclosure provide a weld quality inspection method, including:
  acquiring point cloud data of a target weldment, and converting the point cloud data into a height map, where the target weldment includes a base material, a welding part and a target weld formed by welding the welding part to the base material;
  determining a weld region for characterizing the target weld from the height map;
  analyzing the weld region to obtain a feature parameter of the target weld; and
  obtaining a quality inspection result of the target weld according to the feature parameter.

In the weld quality inspection method provided by the embodiments of the disclosure, the point cloud data of the target weldment is acquired, and the point cloud data is converted into the height map; the weld region for characterizing the target weld from the height map is determined; the weld region is analyzed to obtain the feature parameter of the target weld; and the quality inspection result of the target weld is obtained according to the feature parameter, where the target weldment includes the base material, the welding part and the target weld formed by welding the welding part to the base material. Compared with a solution of adopting a manual inspection method to inspect the weld quality in the prior art, the weld quality inspection method provided by the embodiments of the disclosure can improve the accuracy of a quality inspection result by obtaining the quality inspection result of the target weld based on the machine vision technology and thus avoiding manual participation. For example, the weld quality inspection method provided by the embodiments of the disclosure can be applied to weld quality inspection of peripheral welding to inspect a defect of a weld with an area greater than 0.5 mm$^2$ and a depth greater than 0.2 mm, and has a strong practical application value.

In combination with the first aspect, the embodiments of the disclosure further provide a first alternative implementation of the first aspect: before determining the weld region for characterizing the target weld from the height map, the weld quality inspection method further includes:
  preprocessing the height map, where the preprocessing including filtering processing and/or rectification processing.

In the implementation, before determining the weld region for characterizing the target weld from the height map, the weld quality inspection method further includes: preprocessing the height map, where the preprocessing includes filtering processing and/or rectification processing, to improve the image quality of the height map so as to further improve the accuracy of the quality inspection result.

In conjunction with the first alternative implementation of the first aspect, the embodiments of the disclosure further provide a second alternative implementation of the first aspect: the preprocessing includes rectification processing for preprocessing the height map, which includes:
  performing edge inspection on the height map to determine an edge straight line on a welding side of the target weldment;
  acquiring an included angle between the edge straight line and a preset reference line;
  acquiring a reference point, and obtaining a rotation matrix by taking the reference point as a rotation center and the included angle as a rotation angle; and
  based on the rotation matrix, performing affine transformation on the height map to realize rectification processing on the height map.

In conjunction with the first aspect, the embodiments of the disclosure further provide a third alternative implementation of the first aspect: the determining the weld region for characterizing the target weld from the height map includes:
  selecting a first region of interest from the height map;
  determining a first edge line and a second edge line of the target weld according to height differences between a plurality of pixel points in the first region of interest and a preset reference plane; and
  taking a region image between the first edge line and the second edge line as the weld region for characterizing the target weld.

In conjunction with the third alternative implementation of the first aspect, the embodiments of the disclosure further provide a fourth alternative implementation of the first aspect: determining the first edge line and the second edge line of the target weld according to the height differences between the plurality of pixel points in the first region of interest and the preset reference plane includes:
  drawing a plurality of search straight lines in the first region of interest in a first direction, where the search straight lines are perpendicular to the first direction, and the first direction is a length direction of the first region of interest;

for each of the plurality of search straight lines, determining a first edge point and a second edge point of the target weld on the search straight line according to height differences between a plurality of pixel points discretized on the search straight line and the preset reference plane;

fitting the first edge points on the plurality of search straight lines to obtain the first edge line of the target weld; and fitting the second edge points on the plurality of search straight lines to obtain the second edge line of the target weld.

In conjunction with the fourth alternative implementation of the first aspect, the embodiments of the disclosure further provide a fifth alternative implementation of the first aspect: determining the first edge point and the second edge point of the target weld on the search straight line according to the height differences between the plurality of pixel points discretized on the search straight line and the preset reference plane includes:

for each of the plurality of pixel points discretized on the search straight line, acquiring a height difference between the pixel point and the preset reference plane;

acquiring a pixel point having a maximum height difference from the preset reference plane from the plurality of pixel points discretized on the search straight line to serve as a peak point;

selecting a pixel point which is located in a first orientation of the peak point, has a distance from the peak point that meets a preset distance requirement, and has a minimum height difference from the preset reference plane from the plurality of pixel points discretized on the search straight line to serve as a first auxiliary point, and selecting a sub-pixel point having a minimum height difference from the preset reference plane from a second auxiliary point and a third auxiliary point to serve as a first edge point, where the second auxiliary point is a pixel point adjacent to the first auxiliary point and located in a first orientation of the first auxiliary point; the third auxiliary point is a pixel point adjacent to the first auxiliary point and located in a second orientation of the first auxiliary point; and the second orientation and the first orientation are symmetrical about the peak point; and selecting a pixel point which is located in a second orientation of the peak point, has a height difference from the preset reference plane within a preset height value range, and has a distance from the peak point that is closest to the distance between the first edge point and the peak point, from the plurality of pixel points discretized on the search straight line to serve as a fourth auxiliary point, and selecting a sub-pixel point having a minimum height difference from the preset reference plane from a fifth auxiliary point and a sixth auxiliary point to serve as a second edge point, where the fifth auxiliary point is a pixel point adjacent to the fourth auxiliary point and located in a first orientation of the fourth auxiliary point, and the sixth auxiliary point is a pixel point adjacent to the fourth auxiliary point and located in a second orientation of the fourth auxiliary point.

In conjunction with the first aspect, the embodiments of the disclosure further provide a sixth alternative implementation of the first aspect: analyzing the weld region to obtain the feature parameter of the target weld includes:

setting a plurality of scanning windows in the weld region in a second direction to divide the weld region into a plurality of sub-region images, where the second direction is a length direction of the weld region;

for each of the plurality of sub-region images, obtaining a volume parameter of a sub-target weld characterized by each sub-region image to obtain a plurality of volume parameters; and taking a volume parameter with a minimum value from the plurality of volume parameters as the feature parameter of the target weld.

In conjunction with the sixth alternative implementation of the first aspect, the embodiments of the disclosure further provide a seventh alternative implementation of the above aspect: obtaining the volume parameter of the sub-target weld characterized by the sub-region image includes:

calculating the volume parameter of the sub-target weld characterized by each sub-region image by means of double integral according to a height difference between each pixel point in the sub-region image and the preset reference plane.

In conjunction with the first aspect, the embodiments of the disclosure further provide an eighth alternative implementation of the first aspect: obtaining the quality inspection result of the target weld according to the feature parameter includes:

judging whether the feature parameter is within a preset parameter range;

if the feature parameter is within the preset parameter range, determining that the quality inspection result of the target weld is qualified; and if the feature parameter is out of the preset parameter range, determining that the quality inspection result of the target weld is unqualified.

In conjunction with the first aspect, the embodiments of the disclosure further provide a ninth alternative implementation of the first aspect: obtaining the quality inspection result of the target weld according to the feature parameter includes:

inputting the feature parameter into a preset classification model, and obtaining an output result of the classification model, where the output result includes a first result for characterizing that the quality inspection result of the target weld is qualified, and a second result for characterizing that the quality inspection result of the target weld is unqualified.

In conjunction with the ninth alternative implementation of the first aspect, the embodiments of the disclosure further provide a tenth alternative implementation of the first aspect: before inputting the feature parameter into the preset classification model and obtaining the output result of the classification model, the weld quality inspection method further includes:

acquiring a feature parameter of a standard weld included in each of a first target number of standard weldments as a standard parameter to obtain a first target number of standard parameters;

acquiring a feature parameter of an unqualified weld included in each of a second target number of defective weldments as an unqualified parameter to obtain a second target number of unqualified parameters; and training an initial learning model using the first target number of standard parameters and the second target number of unqualified parameters to obtain the classification model.

In the second aspect, the embodiments of the disclosure provide a weld quality inspection apparatus, including:
- an image acquisition module configured to acquire point cloud data of a target weldment, and convert the point cloud data into a height map, where the target weldment includes a base material, a welding part and a target weld formed by welding the welding part to the base material, the target weld is located on a welding side;
- a positioning module configured to determine a weld region for characterizing the target weld from the height map;
- an image analysis module configured to analyze the weld region to obtain a feature parameter of the target weld; and
- a result acquisition module configured to obtain a quality inspection result of the target weld according to the feature parameter.

The weld quality inspection apparatus provided by the embodiments of the disclosure has the same beneficial effects as the weld quality inspection method provided in the first aspect or any alternative implementation in the first aspect, which will not be repeated here.

In the third aspect, the embodiments of the disclosure provide an electronic device, including a processor and a memory storing a computer program, where the processor is configured to execute the computer program to implement the weld quality inspection method provided in the first aspect or any alternative implementation in the first aspect.

The electronic device provided by the embodiments of the disclosure has the same beneficial effects as the weld quality inspection method provided in the first aspect or any alternative implementation in the first aspect, which will not be repeated here.

In the fourth aspect, the embodiments of the disclosure provide a computer readable storage medium storing a computer program which, when being executed, implements the weld quality inspection method provided in the first aspect or any alternative implementation in the first aspect.

The computer readable storage medium provided by the embodiments of the disclosure has the same beneficial effects as the weld quality inspection method provided in the first aspect or any alternative implementation in the first aspect, which will not be repeated here.

In the fifth aspect, the embodiments of the disclosure provide a weld quality inspection system, including an operation control component, a controller, a data collector and the electronic device provided in the third aspect, where the controller is connected with the operation control component and the data collector, and the data collector is further connected with the electronic device;
- the operation control component is configured to carry a target weldment and operate;
- the controller is configured to control the data collector to collect point cloud data on a welding side of the target weldment in response to the operation control component carrying the target weldment and operating to a target position;
- the data collector is configured to send the point cloud data to the electronic device; and
- the electronic device is configured to acquire the point cloud data of the target weldment, convert the point cloud data into a height map, determine a weld region for characterizing a target weld from the height map, analyze the weld region to obtain a feature parameter of the target weld, and obtain a quality inspection result of the target weld according to the feature parameter, where the target weldment includes a base material, a welding part and the target weld formed by welding the welding part to the base material; and the target weld is located on the welding side.

The weld quality inspection system provided by the embodiments of the disclosure has the same beneficial effects as the weld quality inspection method provided in the first aspect or any alternative implementation of the first aspect, which will not be repeated here.

BRIEF DESCRIPTION OF DRAWINGS

In order to more clearly explain the technical solutions of the embodiments of the disclosure, drawings required to be used in the embodiments of the disclosure will be briefly introduced below. It should be understood that the following drawings merely show some embodiments of the disclosure, so they should not be regarded as limiting the scope. Those having ordinary skill in the art may also obtain other relevant drawings according to these drawings without contributing creative labor.

Figure 1:
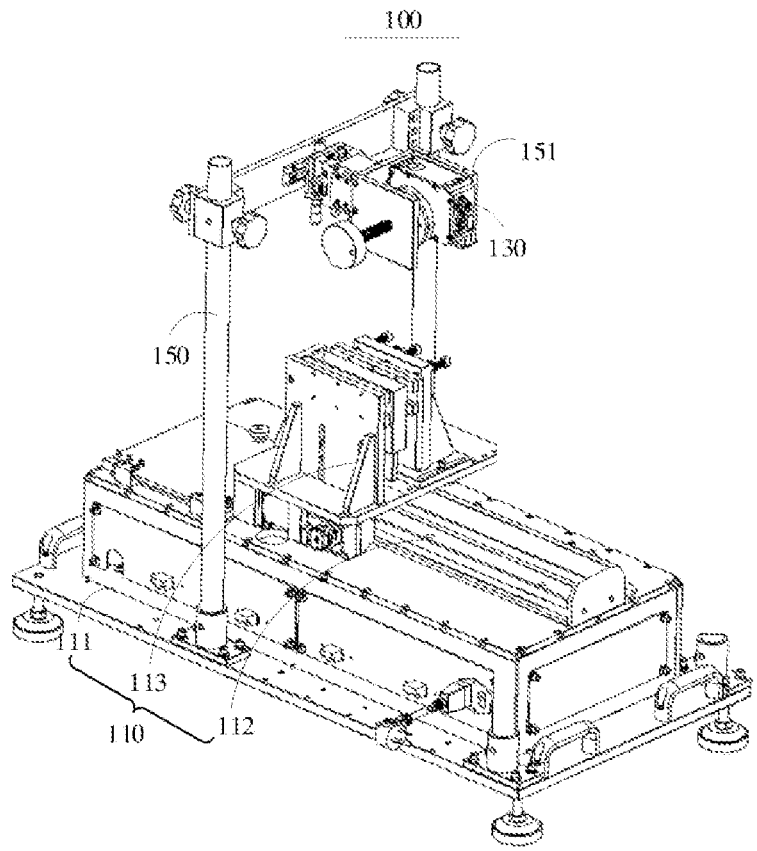
FIG. 1 is a structural schematic diagram of a weld quality inspection system provided by the embodiments of the disclosure.

Reference numerals: 100—weld quality inspection system; 110—operation control component; 111—substrate; 112—sliding rail; 113—clamp; 114—guide control component; 120—controller; 130—data collector; 140—electronic device; 150—first mounting frame; 151—clamping portion; 200—power battery; 210—battery housing; 211—opening;

220—battery cover plate; 221—external side surface; 230—target weld; 300—weld quality inspection apparatus; 310—image acquisition module; 320—positioning module; 330—image analysis module; 340—result acquisition module.

DETAILED DESCRIPTION

In order to make the objects, technical solutions and advantages of the disclosure clearer, the technical solutions in the embodiments of the disclosure will be described with reference to the drawings in the embodiments of the disclosure. In addition, it should be noted that similar reference numerals and letters indicate similar items in the following drawings, so once a certain item is defined in one drawing, it is not necessary to further define and explain the item in the subsequent drawings.

Figure 2:
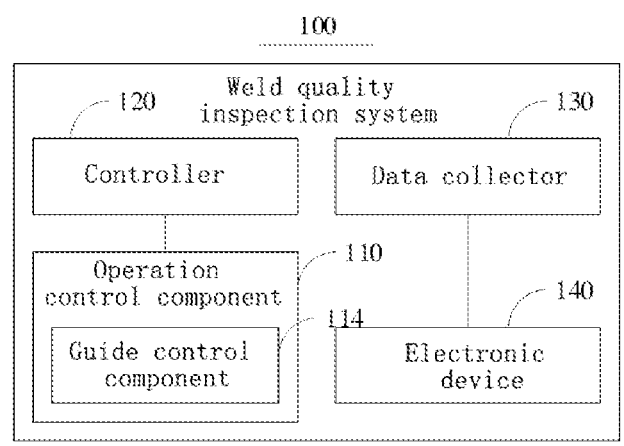
FIG. 2 is a schematic structural block diagram of a weld quality inspection system provided by the embodiments of the disclosure.

Referring to FIGS. 1 and 2, in an embodiment of the disclosure, a weld quality inspection system 100 includes an operation control component 110, a controller 120, a data collector 130 and an electronic device 140, where the controller 120 is connected with the operation control component 110 and the data collector 130, and the data collector 130 is further connected with the electronic device 140.

The operation control component 110 is configured to carry a target weldment and operate.

In the embodiments of the disclosure, the operation control component 110 may include a substrate 111, a sliding rail 112, a clamp 113 and a guide control component 114, where the sliding rail 112 is arranged on the substrate 111; the clamp 113 is arranged on the sliding rail 112 and may operate in a length direction of the sliding rail 112 under the control of the guide control component 114; the clamp 113 is configured to clamp the target weldment; and a welding side of the target weldment is arranged away from the sliding rail 112.

The controller 120 is configured to control the data collector 130 to collect point cloud data on the welding side of the target weldment when the operation control component 110 carries the target weldment and operates to a target position.

In the embodiments of the disclosure, the controller 120 may be, but not limited to, a programmable logic controller (PLC) 120. In the embodiments of the disclosure, the controller 120 may be specifically connected with the guide control component 114, and is configured to control the clamp 113 to operate in the length direction of the sliding rail 112 through the guide control component 114 when the target weldment is clamped by the clamp 113 and the welding side is arranged away from the sliding rail 112, and control the data collector 130 to collect the point cloud data on the welding side of the target weldment when the clamp 113 clamps the target weldment and operates to the target position. In addition, in the embodiments of the disclosure, the controller 120 may judge whether the operation control component 110 carries the target weldment and operates to the target position according to an operation time duration and an operation speed of the control component carrying the target weldment.

The data collector 130, in the embodiments of the disclosure, may be a laser profile sensor, for example, an LMI2520 line profile sensor. During actual implementation, the data collector 130 may be arranged above the substrate 111 through the first mounting frame 150. Specifically, the data collector 130 may be clamped on the clamping portion 151 arranged on the first mounting frame 150.

The data collector 130 is configured to send the point cloud data to the electronic device 140.

The electronic device 140 is configured to acquire the point cloud data of the target weldment, convert the point cloud data into the height map, determine a weld region for characterizing a target weld from the height map, analyze the weld region to obtain feature parameter of the target weld, and obtain a quality inspection result of the target weld according to the feature parameter, where the target weldment includes a base material, a welding part and a target weld formed by welding the welding part to the base material.

The electronic device 140, in the embodiments of the disclosure, may be a server, for example, a network server, a database server or the like, or may be a terminal device, for example, an industrial computer. Structurally, the electronic device 140 may include a processor and a memory.

The processor and the memory are electrically connected directly or indirectly to realize data transmission or interaction. For example, these elements may be electrically connected with each other through one or more communication buses or signal lines. The weld quality inspection apparatus includes at least one software module that may be stored in the memory in the form of software or firmware or solidified in an operating system (OS) of the electronic device 140. The processor is configured to execute executable modules stored in the memory, for example, software functional modules, computer programs, etc. included in the weld quality inspection apparatus, to implement the weld quality inspection method.

The processor may execute a computer program after receiving an execution instruction, wherein the processor may be an integrated circuit chip with the signal processing capability. The processor may also be a general-purpose processor, for example, a digital signal processor (DSP), an application specific integrated circuit (ASIC), a discrete gate or transistor logic device, or a discrete hardware component, and may implement or execute the methods, steps and logic block diagrams in the embodiments of the disclosure. In addition, the general-purpose processor may be a microprocessor, any conventional processor or the like.

The memory may be, but not limited to, a random access memory (RAM), a read only memory (ROM), a programmable read-only memory (PROM), an erasable programmable read-only memory (EPROM), or an electric erasable programmable read-only memory (EEPROM). The memory is configured to store a program, and the processor executes the program after receiving an execution instruction.

It should be understood that the above-described structure is only illustrative, and the electronic device 140 provided by the embodiments of the disclosure may further have fewer or more components than those described above, or have a different configuration from those described above.

Figure 3:
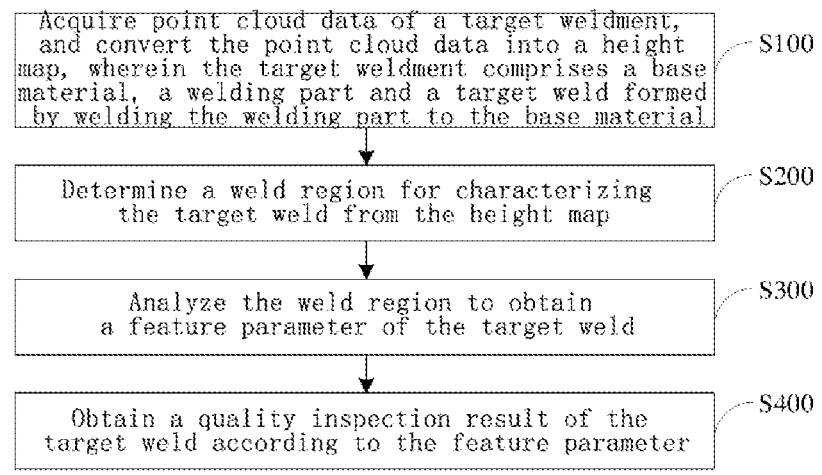
FIG. 3 is a flowchart of steps of a weld quality inspection method provided by the embodiments of the disclosure.

Referring to FIG. 3, which is a flowchart of a weld quality inspection method provided by the embodiments of the disclosure, the method is applied to the electronic device shown in FIG. 2. It should be noted that the weld quality inspection method provided by the embodiments of the disclosure is not limited by the sequence shown in FIG. 3 and below. Specific processes and steps of the weld quality inspection method provided by the embodiments of the disclosure will be described below with reference to FIG. 3.

In step S100, point cloud data of a target weldment is acquired and is converted into a height map, where the target weldment includes a base material, a welding part and a target weld formed by welding the welding part to the base material.

Figure 4:
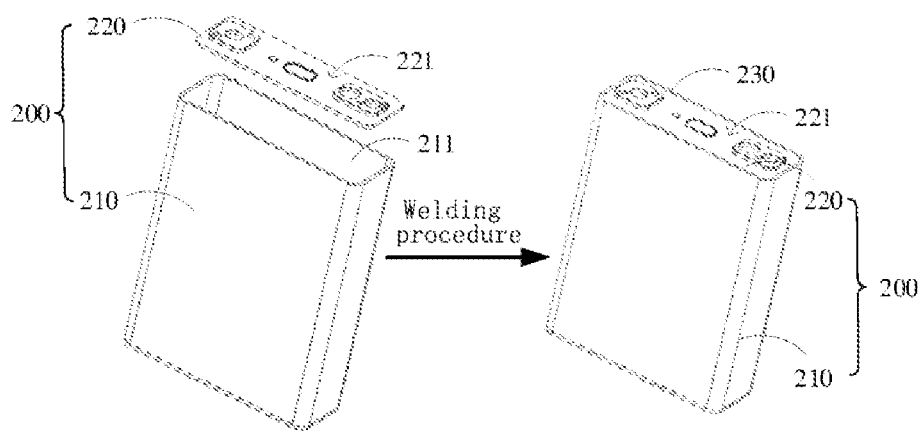
FIG. 4 is a schematic diagram of welding assembly of a power battery provided by the embodiments of the disclosure.

In the embodiments of the disclosure, the target weldment may be, but not limited to, a product in petrochemical industry, automobile industry, shipping industry, electric energy industry, packaging box manufacturing industry and other industries. With reference to FIG. 4, taking a power battery 200 as a target weldment an example, the base material may be the battery housing 210, the welding part may be the battery cover plate 220, and the battery housing 210 may has a structure of rectangular opening 211. The battery cover plate 220 is matched with the opening 211 in the battery housing 210 in shape and size. When the battery cover plate 220 is installed at the opening 211 of the battery housing 210, the external side surface 221 of the battery cover plate 220 is flush with the opening 211 of the battery housing 210, but it is still necessary to weld the battery cover plate 220 to the battery housing 210 through a welding procedure to achieve fixation. The target weld 230 formed by welding the battery cover plate 220 to the battery housing 210 is just a joint formed after the external side surface 221 of the battery cover plate 220 is flush with the opening 211 of the battery housing 210.

In addition, it should be noted that in the embodiments of the disclosure, the height map may be understood as a gray map converted from the point cloud data. For each pixel point in the height map, a height value of the pixel point may be obtained according to a gray value of the pixel point, and the height value of each pixel point may be understood as a value of a distance between a position on the target weldment characterized by each pixel point and the data collector.

In step S200, a weld region for characterizing the target weld is determined from the height map.

In the embodiments of the disclosure, in order to improve the image quality of the height map, before step S200 is executed, step S001 may be further included: preprocessing the height map; and the preprocessing includes filtering processing and/or rectification processing.

In the embodiments of the disclosure, the filtering processing may be, but not limited to, mean filtering, median filtering, Gaussian filtering, bilateral filtering, etc. Taking Gaussian filtering as an example, the principle is to scan each pixel point in the height map through a preset mask, and replace a gray value of a center pixel point in a region, where the mask is located, with the weighted average gray value of all the pixel points in the region where the mask is located, so as to smooth the height map. During actual implementation, an adopted Gaussian filtering function may be a Gaussian Blur function of OpenCV, and the mask may have 5*5 pixel points.

The rectification processing, in the embodiments of the disclosure, as an alternative implementation, may be implemented by: performing edge inspection on the height map to determine an edge straight line on the welding side of the target weldment; acquiring an included angle between the edge straight line and a preset reference line; acquiring a reference point, and obtaining a rotation matrix by taking the reference point as a rotation center and the included angle as a rotation angle; and finally, based on the rotation matrix, performing affine transformation on the height map to realize rectification processing on the height map. During actual implementation, a plurality of weldment edge points may be acquired in a second region of interest of the height map with preset search parameters through a Sobel operator, and then the plurality of weldment edge points are fitted to determine the edge straight line on the welding side of the target weldment. The preset reference line may be any vertical line or horizontal line in the height map, and the reference point may be any pixel point in the height map, for example, a center point of the region where the target weldment is located in the height map.

Figure 5:
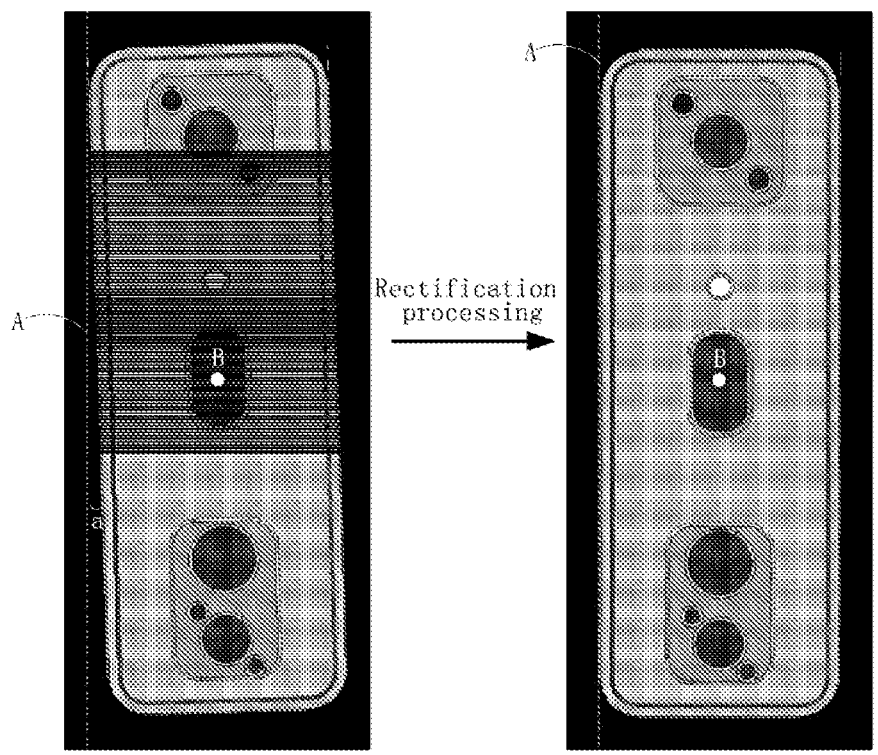
FIG. 5 is a schematic diagram of a process of rectifying a height map provided by the embodiments of the disclosure.

Taking the process of rectifying the height map shown in FIG. 5 as an example, by taking the preset reference line as a vertical line A in the height map, the reference point as a center point B in the region where the target weldment is located in the height map, the reference point as a rotation center, and the value of the included angle $\alpha$ between the edge straight line and the preset reference line as a rotation angle, a rotation matrix is obtained. Finally, based on the rotation matrix, affine transformation is performed on the height map to realize rectification processing on the height map.

In addition, it should be noted that in the embodiments of the disclosure, the region of interest refers to a region to be processed which is outlined by a rectangular frame, a circular frame, an elliptical frame, an irregular polygonal frame or frames of other shape from the processed image in the process of machine vision and image processing. During actual implementation, various operators and functions commonly utilized in machine vision software such as Halcon, OpenCV and Matlab may be utilized to obtain a second region of interest. In addition, in the embodiments of the disclosure, the plurality of weldment edge points may be, but not limited to, 3, 5, or 10 points. After being acquired, the plurality of weldment edge points may be fitted by means of the least square method, so as to determine the edge straight line on the welding side of the target weldment.

By preprocessing the height map, the image quality of the height map can be improved. In this way, when the subsequent steps S200, S300 and S400 are executed to finally obtained the quality inspection result of the target weld, the accuracy of the quality inspection result can be further improved.

Step S200, in the embodiments of the disclosure, as an alternative implementation, may include step S210, step S220 and step S230.

In step S210, the first region of interest is selected from the height map.

Figure 6:
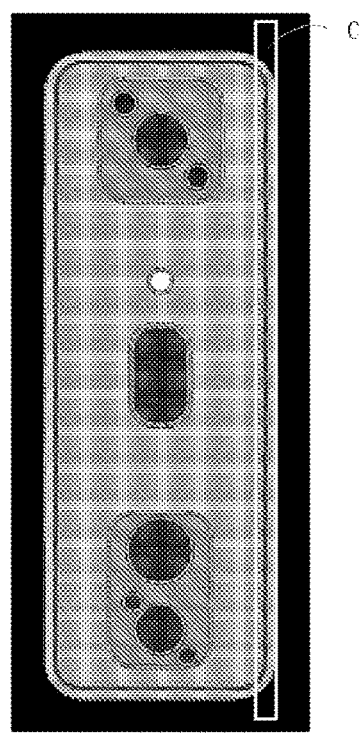
FIG. 6 is a schematic diagram of a position of a first region of interest in a height map provided by the embodiments of the disclosure.

Taking the height map shown in FIG. 6 as an example, the height map is a height map on the welding side of the target weldment. It can also be understood that the height map is a top view of the target weldment. In addition, in the embodiments of the disclosure, the first region of interest C selected from the height map may be a region to be processed which is outlined by the rectangular frame; and the region to be processed includes a welding region image.

In step S220, a first edge line and a second edge line of the target weld are determined according to height differences between a plurality of pixel points in the first region of interest and a preset reference plane.

In the embodiments of the disclosure, for each pixel point in the first region of interest, a height value of the pixel point may be acquired according to a gray value of the pixel point; the height value of the pixel point may be understood as a distance between a corresponding position of the pixel point on the target weldment and the data collector; and the height difference between the pixel point and the preset reference plane may be understood as the difference between the height value of the pixel point on the target weldment and the height value of the preset reference plane. Similarly, it can be understood that the height value of the preset reference plane is the value of the distance between the preset reference plane and the data collector. Further, Step S220, in the embodiments of the disclosure, as an alternative implementation, may include step S221, step S222, step S223 and step S224.

In step S221, a plurality of search straight lines are drawn in the first region of interest in a first direction, where the search straight lines are perpendicular to the first direction, and the first direction is a length direction of the first region of interest.

Figure 7:
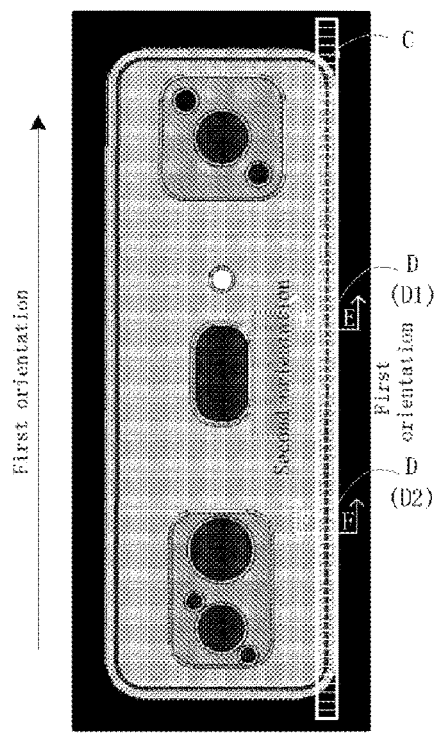
FIG. 7 is a schematic diagram of a drawing mode of multiple search straight lines provided by the embodiments of the disclosure.

Referring to FIG. 7, in the embodiments of the disclosure, a plurality of search straight lines D may be drawn in the first region of interest C in the first direction with a first preset length as an interval distance, and the search straight lines D are perpendicular to the first direction, where the first direction is a length direction of the first region of interest C, and the first preset length may be, but not limited to, 10 pixel points, 20 pixel points and 30 pixel points.

In step S222, for each of the plurality of search straight lines, a first edge point and a second edge point of the target weld are determined on the search straight line according to a height difference between the plurality of pixel points discretized on the search straight line and the preset reference plane.

Determining the first edge point and the second edge point of the target weld on the search straight line according to the height difference between the plurality of pixel points discretized on the search straight line and the preset reference plane in step S222, as an alternative implementation in the embodiments of the disclosure, may include: for each of the plurality of pixel points discretized on the search straight line, acquiring a height difference between the pixel point and the preset reference plane; acquiring a pixel point having a maximum height difference from the preset reference plane from the plurality of pixel points discretized on the search straight line to serve as a peak point; selecting a pixel point which is located in a first orientation of the peak point, has a distance from the peak point that meets a preset distance requirement, and has a minimum height difference from the preset reference plane from the plurality of pixel points discretized on the search straight line to serve as a first auxiliary point, and selecting a sub-pixel point having a minimum height difference from the preset reference plane from a second auxiliary point and a third auxiliary point to serve as a first edge point, where the second auxiliary point is a pixel point adjacent to the first auxiliary point and located in a first orientation of the first auxiliary point, the third auxiliary point is a pixel point adjacent to the first auxiliary point and located in a second orientation of the first auxiliary point, and the second orientation and the first orientation are symmetrical about the peak point; and finally, selecting a pixel point which is located in a second orientation of the peak point, has a height difference from the preset reference plane that is within a preset height value range, and has a distance from the peak point that is closest to the distance between the first edge point and the peak point from the plurality of pixel points discretized on the search straight line to serve as a fourth auxiliary point, and selecting a sub-pixel point having a minimum height difference from the preset reference plane from a fifth auxiliary point and a sixth auxiliary point to serve as a second edge point, where the fifth auxiliary point is a pixel point adjacent to the fourth auxiliary point and located in a first orientation of the fourth auxiliary point, and the sixth auxiliary point is a pixel point adjacent to the fourth auxiliary point and located in a second orientation of the fourth auxiliary point; and the preset distance requirement and the preset height value range may be specifically set according to product requirements of the target weldment, which will not be specifically limited in the embodiments of the disclosure. In addition, it should be noted that in the embodiments of the disclosure, the number of sub-pixel points divided between the first auxiliary point and the second auxiliary point, the number of sub-pixel points divided between the first auxiliary point and the third auxiliary point, the number of sub-pixel points divided between the fourth auxiliary point and the fifth auxiliary point, and the number of sub-pixel points divided between the fourth auxiliary point and the sixth auxiliary point are not limited.

It should be noted that in the embodiments of the disclosure, the first orientation may be an orientation in which the peak point faces the outside of the target weld, or may be an orientation in which the peak point faces the inside of the target weld. If the first orientation is an orientation in which the peak point faces the outside of the target weld, the first edge point is an outer edge point of the target weld, and the second edge point is an inner edge point of the target weld; and if the first orientation is an orientation in which the peak point faces the inside of the target weld, the first edge point is an inner edge point of the target weld, and the second edge point is an outer edge point of the target weld.

In addition, it should be noted that in the embodiments of the disclosure, the preset reference plane may be a region with a gentle height on a welding part on the target weldment. Taking a power battery as the target weldment as an example, the preset reference plane may be a region with a gentle height on a battery cover plate. It can further be understood that the preset reference plane may be a gentle region where no target weld is formed on the battery cover plate, and the region is coplanar with the bottom of the target weld.

Figure 8:
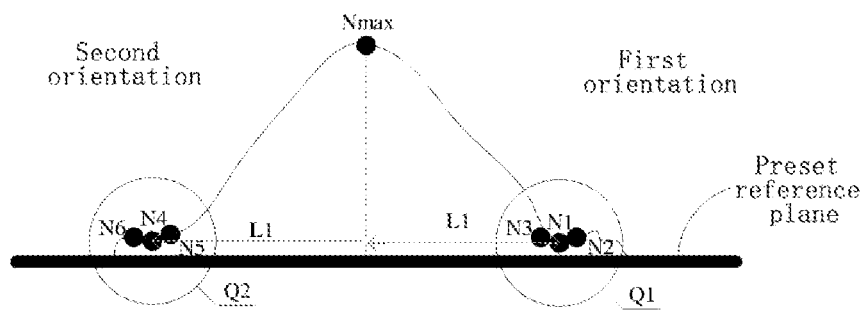
FIG. 8 is a sectional view of a target weld provided by the embodiments of the disclosure.
Figure 9:
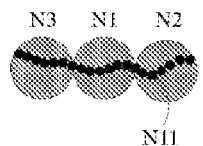
FIG. 9 is an enlarged view of Q1 in FIG. 8.
Figure 10:
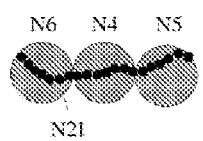
FIG. 10 is an enlarged view of Q2 in FIG. 8.

Hereinafter, the specific processes and steps of step S222 will be further described with reference to FIGS. 8, 9 and 10, where FIG. 9 is an enlarged view of Q1 in FIG. 8, and FIG. 10 is an enlarged view of Q2 in FIG. 8.

Taking the search straight line D1 shown in FIG. 7 as an example, firstly, for each of a plurality of pixel points discretized on the search straight line D1, a height difference between the pixel point and the preset reference plane is acquired. For convenience of understanding, in the embodiments of the disclosure, an E-E sectional view of a corresponding target weld in the region of interest shown in FIG. 7, that is, a sectional view of a corresponding target weld at the position of the search straight line D1, may be simulated, as shown in FIG. 8.

After, for each of the plurality of pixel points discretized on the search straight line D1, the height difference between the pixel point and the preset reference plane is acquired, the pixel point having the maximum height difference from the preset reference plane may be acquired from the plurality of pixel points discretized on the search straight line D1 to serve as the peak point. For convenience of description, in the embodiments of the disclosure, the peak point may be denoted as Nmax.

The pixel point which is located in the first orientation of the peak point Nmax, has the distance from the peak point Nmax that meets the preset distance requirement, and has the minimum height difference from the preset reference plane is selected from the plurality of pixel points discretized on the search straight line D1 to serve as the first auxiliary point; and a sub-pixel point having a minimum height difference from the preset reference plane is selected from the second auxiliary point and the third auxiliary point to serve as the first edge point. Taking the first orientation as an orientation in which the peak point Nmax faces the outside of the target weld as an example, that is, taking a right orientation of the peak point Nmax in FIGS. 7 and 8 as an example, a pixel point which is located in the right orientation of the peak point Nmax, has a distance from the peak point Nmax that meets a preset distance requirement, and has a minimum height difference from the preset reference plane is selected from the plurality of pixel points discretized on the search straight line D1 to serve as a first auxiliary point, denoted as N1; and then a sub-pixel point having a minimum height difference from the preset reference plane is selected from the second auxiliary point N2 and the third auxiliary point N3 to serve as a first edge point, denoted as N11.

Finally, a pixel point which is located in a second orientation of the peak point Nmax, has a height difference from the preset reference plane within a preset height value range, and has distance L1 from the peak point that is closest to the distance between the first edge point N11 and the peak point Nmax, is selected from the plurality of pixel points discretized on the search straight line D1 to serve as a fourth auxiliary point, denoted as N4; and a sub-pixel point having a minimum height difference from the preset reference plane is selected from a fifth auxiliary point N5 and a sixth auxiliary point N6 to serve as a second edge point, denoted as N21.

In step S223, the first edge points on the plurality of search straight lines are fitted to obtain a first edge line of the target weld.

In step S224, the second edge points on the plurality of search straight lines are fitted to obtain a second edge line of the target weld.

It should be noted that in the embodiments of the disclosure, the first edge line of the target weld may be a straight line or a curved line; and similarly, the second edge line of the target weld may be a straight line or a curved line, which will not be specifically limited in the embodiments of the disclosure.

In step S230, a region image between the first edge line and the second edge line is taken as the weld region for characterizing the target weld.

In step S300, the weld region is analyzed to obtain a feature parameter of the target weld.

In the embodiments of the disclosure, the feature parameter of the target weld may be understood as the overall volume parameters of the target weld, and the overall volume parameters of the target weld may be obtained by means of double integral calculation according to the height difference between each pixel point in the weld region and the preset reference plane. However, in order to further improve the accuracy of the quality inspection result, step S300, in the embodiments of the disclosure, as an alternative implementation, may include step S310, step S320 and step S330.

In step S310, a plurality of scanning windows are set in the weld region in a second direction to divide the weld region into a plurality of sub-region images, where the second direction is a length direction of the weld region.

Figure 11:
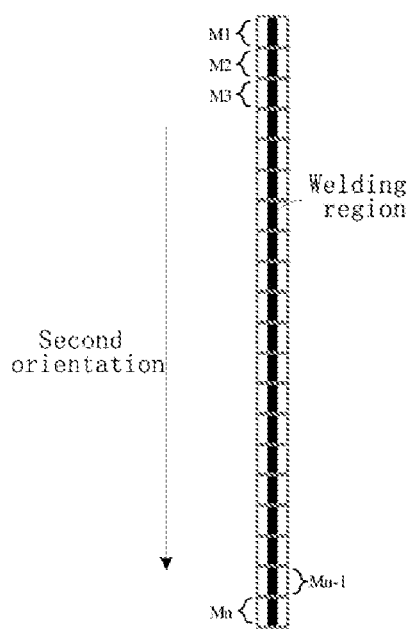
FIG. 11 is a schematic diagram of a setting of a scanning window provided by the embodiments of the disclosure.
Figure 12:
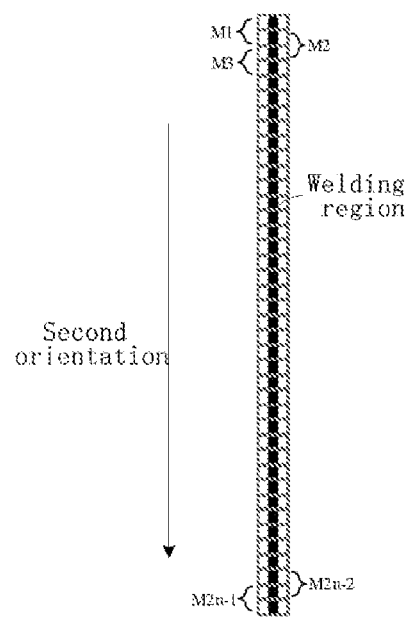
FIG. 12 is a schematic diagram of another setting of a scanning window provided by the embodiments of the disclosure.

In the embodiments of the disclosure, a length of each scanning window may be specifically set according to the product requirements of the target weldment, which is not specifically limited in the embodiments of the disclosure. In addition, in the embodiments of the disclosure, the scanning window may be square or rectangular, which is also not limited in the embodiments of the disclosure as well. With reference to FIG. 11, after the length of a scanning window is set, a plurality of scanning windows may be set in the weld region in a second direction with a step of a second preset length value and are characterized as M1, M2, M3 . . . Mn−1, Mn respectively, to divide the weld region into a plurality of sub-region images; or with reference to FIG. 12, after the length of a scanning window is set, a plurality of scanning windows may be set in the weld region in a second direction with a step of a second preset length and are characterized as M1, M2, M3 . . . M2n−2, M2n−1 respectively, where the second direction is a length direction of the weld region, the second preset length may be equal to the length of the scanning window (as shown in FIG. 11), or may be ½ of the length of the scanning window (as shown in FIG. 12), or other values.

In step S320, for each of the plurality of sub-region images, a volume parameter of a sub-target weld characterized by the sub-region image is obtained, to obtain a plurality of volume parameters.

Figure 13:
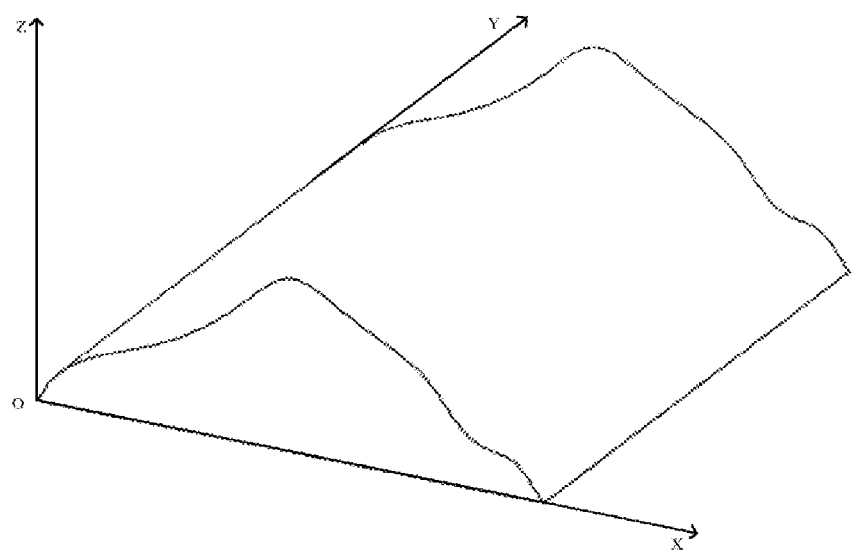
FIG. 13 is an auxiliary explanatory diagram of a calculation process of a volume parameter of a sub-target weld provided by the embodiments of the disclosure.

In the embodiments of the disclosure, for each of a plurality of sub-region images, a volume parameter of a sub-target weld characterized by the sub-region image may be calculated by means of double integral according to the height difference between each pixel point in the sub-region image and the preset reference plane. Taking a sub-region image divided in any scanning window shown in FIG. 11 or FIG. 12 as an example, a three-dimensional coordinate system O-XYZ, in which the X axis and Y axis are located on the preset reference plane, the X-axis direction is a width direction of the weld region, the Y-axis direction is a second direction (that is, a length direction of the weld region), and the Z axis is perpendicular to the preset reference plane, is established, specifically as shown in FIG. 13. In this way, the Z-axis coordinate value of any pixel point in the sub-region image is the height difference between the pixel point and the preset reference plane. Based on this, step S320, in the embodiments of the disclosure, as a first alternative implementation, may be implemented by calculating the volume parameter of the sub-target weld characterized by the sub-region image through the following double integral calculation logic:

$$\int\int_D f(x, y)dxdy$$

where f(x, y) is a sectional area function of the sub-target weld on the Z axis, and D is an integral region, that is, a region where the sub-region image is located.

Figure 14:
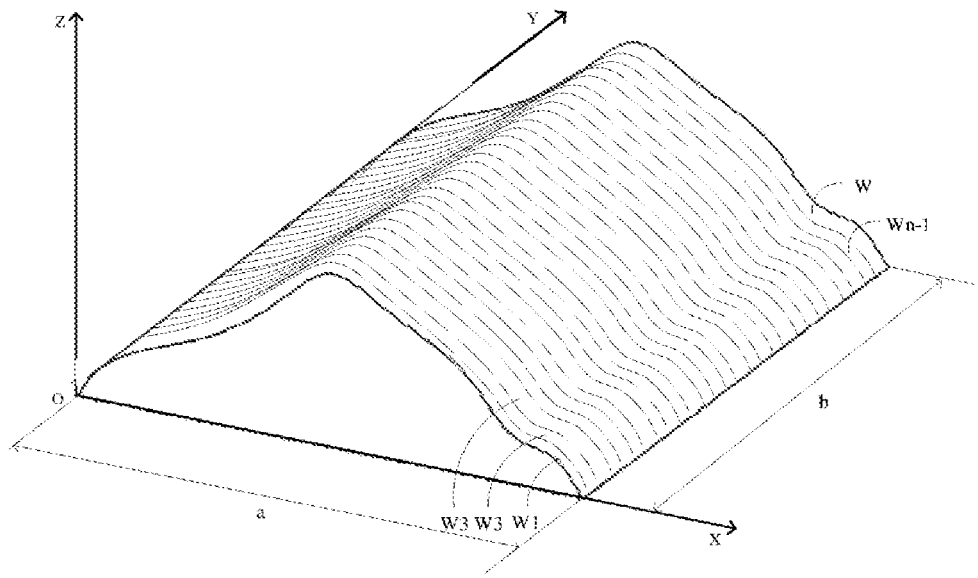
FIG. 14 is an auxiliary explanatory diagram of a calculation process of a volume parameter of another sub-target weld provided by the embodiments of the disclosure.

With reference to FIG. 14, step S320, in the embodiments of the disclosure, as a second alternative implementation, may be implemented by: dividing the sub-region image into a plurality of integral units (characterized as W1, W2, W3, . . . Wn−1 respectively) in the Y-axis direction by taking one pixel point as a unit, and then, for each integral unit, calculating a volume parameter of a weld unit characterized by the integral unit through the following first integral calculation logic:

$$\int_0^a f(x)dx$$

where f(x) is a height function of the weld unit on the Z axis, and a is a length value of the scanning window in the X-axis direction.

After obtaining the volume parameter of the weld unit characterized by each of the plurality of integral units through the first integral calculation logic, a volume parameter of a sub-target weld characterized by the sub-region image is calculated through the following second integral calculation logic:

$$\int_0^b f(y)dy$$

where f(y) is a volume parameter of the weld unit characterized by the integral unit in the Y-axis direction. It can also be understood that f(y) is a sectional area function of the sub-target weld on the Y axis, and b is a length value of the scanning window in the Y-axis direction.

In step S330, a volume parameter with a minimum value from the plurality of volume parameters is taken as the feature parameter of the target weld.

Figure 15:
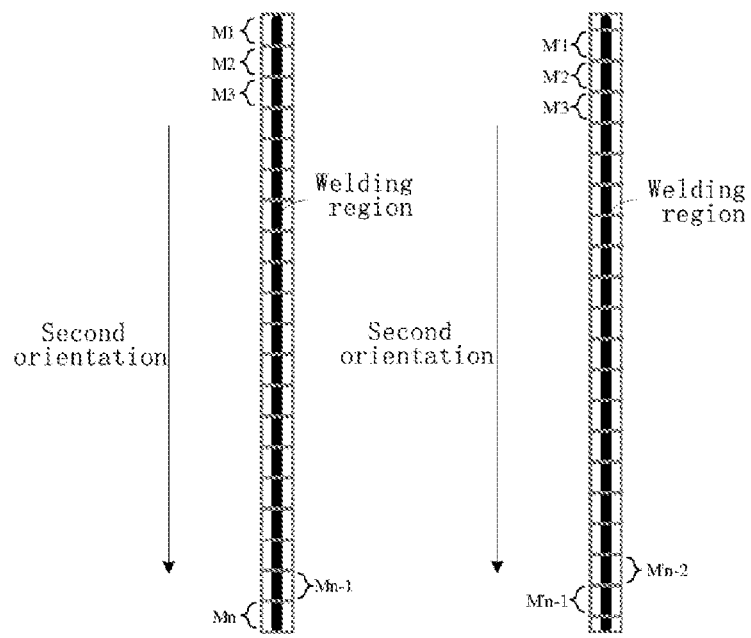
FIG. 15 is a schematic diagram of another setting of a scanning window provided by the embodiments of the disclosure.

It should be noted that if the second preset length is ½ of or less than the length of the scanning window, the volume parameter with the minimum value from the plurality of volume parameters may be directly utilized as the feature parameter of the target weld. If the second preset length is equal to the length of the scanning window, after the plurality of volume parameters are obtained by executing step S310 and step S320, a center position of a first scanning window obtained when step S310 is executed may be utilized as a window start position. A plurality of scanning windows are set in the second direction again to divide the weld region into a plurality of sub-region images. For each of the plurality of sub-region images, a volume parameter of a sub-target weld characterized by each sub-region image is obtained to obtain a plurality of volume parameters again. A plurality of scanning windows (characterized as M1, M2, M3, . . . Mn–1, Mn respectively) are set in the process of obtaining the plurality of volume parameters for the first time, and a plurality of scanning windows (characterized as M'1, M'2, M'3 . . . M'n–1, M'n respectively) are set in the process of obtaining the plurality of volume parameters for the second time, as shown in FIG. 15. Finally, among the plurality of volume parameters during the above two processes, the volume parameter with the minimum value is taken as the feature parameter of the target weld.

In step S400, a quality inspection result of the target weld is obtained according to the feature parameter.

Step S400, in the embodiments of the disclosure, as a first alternative implementation, may be implemented by: judging whether the feature parameter is within a preset parameter range; if the feature parameter is within the preset parameter range, determining that the quality inspection result of the target weld is qualified; and if the feature parameter is out of the preset parameter range, determining that the quality inspection result of the target weld is unqualified. The preset parameter range may be specifically set according to product requirements of the target weldment, which will not be specifically limited in the embodiments of the disclosure.

To further improve the accuracy of the quality inspection result, step S400, in the embodiments of the disclosure, as a second alternative implementation, may be implemented by: inputting the feature parameter into a preset classification model, and obtaining an output result of the classification model, where the output result includes a first result for characterizing that the quality inspection result of the target weld is qualified; and a second result for characterizing that the quality inspection result of the target weld is unqualified.

Based on the above description, before inputting the feature parameter into the preset classification model and obtaining the output result of the classification model, the weld quality inspection method provided by the embodiments of the disclosure may further include: acquiring a feature parameter of a standard weld included in each of a first target number of standard weldments to serve as a standard parameter, to obtain a first target number of standard parameters; acquiring a feature parameter of an unqualified weld included in each of a second target number of defective weldments to serve as an unqualified parameter, to obtain a second target number of unqualified parameters; and training an initial learning model using the first target number of standard parameters and the second target number of unqualified parameters to obtain the classification model. It should be noted that in the process of training the initial learning model, weld region profile parameter of the standard weld in each standard weldment and weld region profile parameter of the unqualified weld in each defective weldment may be utilized. In addition, in the embodiments of the disclosure, the initial learning model may be a support vector machine (SVM).

Figure 16:
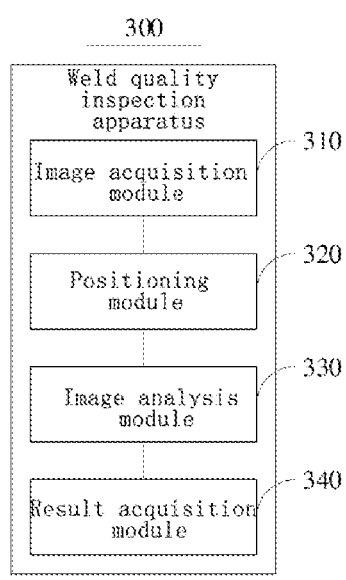
FIG. 16 is a structural schematic diagram of a weld quality inspection apparatus provided by the embodiments of the disclosure.

Based on the same invention concept as the above weld quality inspection method, the embodiments of the disclosure further provide a weld quality inspection apparatus 300. Referring to FIG. 16, the weld quality inspection apparatus 300 provided by the embodiments of the disclosure includes an image acquisition module 310, a positioning module 320, an image analysis module 330 and a result acquisition module 340.

The image acquisition module 310 is configured to acquire point cloud data of a target weldment, and convert the point cloud data into a height map, where the target weldment includes a base material, a welding part and a target weld formed by welding the welding part to the base material.

For the description of the image acquisition module 310, please specifically refer to the detailed description of step S100 shown in FIG. 3, that is, step S100 may be executed by the image acquisition module 310.

The positioning module 320 is configured to determine a weld region for characterizing the target weld from the height map.

For the description of the positioning module 320, please specifically refer to the detailed description of step S200 shown in FIG. 3, that is, step S200 may be executed by the positioning module 320.

The image analysis module 330 is configured to analyze the weld region to obtain a feature parameter of the target weld.

For the description of the image analysis module 330, please specifically refer to the detailed description of step S300 shown in FIG. 3, that is, step S300 may be executed by the image analysis module 330.

The result acquisition module 340 is configured to obtain a quality inspection result of the target weld according to the feature parameter.

The obtaining the quality inspection result of the target weld according to the feature parameter may include:
 judging whether the feature parameter is within a preset parameter range;
 if the feature parameter is within the preset parameter range, determining that the quality inspection result of the target weld is qualified; and if the feature parameter is out of the preset parameter range, determining that the quality inspection result of the target weld is unqualified.

The judging whether the feature parameter is within a preset parameter range may include:

inputting the feature parameter into a preset classification model, and obtaining an output result of the classification model, where the output result includes a first result for characterizing that the quality inspection result of the target weld is qualified; and a second result for characterizing that the quality inspection result of the target weld is unqualified.

Based on this, before inputting the feature parameter into the preset classification model and obtaining the output result of the classification model, the weld quality inspection method further includes:

acquiring a feature parameter of a standard weld included in each of a first target number of standard weldments to serve as a standard parameter, to obtain a first target number of standard parameters;

acquiring a feature parameter of an unqualified weld included in each of a second target number of defective weldments to serve as an unqualified parameter, to obtain a second target number of unqualified parameters; and training an initial learning model using the first target number of standard parameters and the second target number of unqualified parameters to obtain the classification model.

For the description of the result acquisition module 340, please specifically refer to the detailed description of step S400 shown in FIG. 3, that is, step S400 may be executed by the result acquisition module 340.

The weld quality inspection apparatus 300 provided by the embodiments of the disclosure may further include a preprocessing module.

The preprocessing module is configured to preprocess the height map; and preprocessing includes filtering processing and/or rectification processing.

In case that the preprocessing includes rectification processing, the preprocessing the height map may include:

performing edge inspection on the height map to determine an edge straight line on a welding side of the target weldment;

acquiring an included angle between the edge straight line and a preset reference line;

acquiring a reference point, and obtaining a rotation matrix by taking the reference point as a rotation center and the included angle as a rotation angle; and based on the rotation matrix, performing affine transformation on the height map to realize rectification processing on the height map.

For the description of the preprocessing module, please specifically refer to the detailed description of step S001 in the related embodiment of the above weld quality inspection method, that is, step S001 may be executed by the preprocessing module.

In the embodiments of the disclosure, the positioning module 320 may include a region selection unit, an edge line determination unit and an image acquisition unit.

The region selection unit is configured to select a first region of interest from the height map.

For the description of the region selection unit, please specifically refer to the detailed description of step S210 in the related embodiment of the above weld quality inspection method, that is, step S210 may be executed by the region selection unit.

The edge line determination unit is configured to determine a first edge line and a second edge line of the target weld according to height differences between a plurality of pixel points in the first region of interest and a preset reference plane.

For the description of the edge line determination unit, please specifically refer to the detailed description of step S220 in the related embodiment of the above weld quality inspection method, that is, step S220 may be executed by the edge line determination unit.

The image acquisition unit is configured to take a region image between the first edge line and the second edge line as the weld region for characterizing the target weld.

For the description of the image acquisition unit, please specifically refer to the detailed description of step S230 in the related embodiment of the above weld quality inspection method, that is, step S230 may be executed by the image acquisition unit.

In the embodiments of the disclosure, the edge line determination unit may include a drawing subunit, an edge point determination subunit, a first edge line determination subunit and a second edge line determination subunit.

The drawing subunit is configured to draw a plurality of search straight lines in the first region of interest in a first direction, where the search straight lines are perpendicular to the first direction, and the first direction is a length direction of the first region of interest.

For the description of the drawing subunit, please specifically refer to the detailed description of step S221 in the related embodiment of the above weld quality inspection method, that is, step S221 may be executed by the drawing subunit.

The edge point determination subunit is configured to, for each of the plurality of search straight lines, determine a first edge point and a second edge point of the target weld on the search straight line according to height differences between a plurality of pixel points discretized on the search straight line and the preset reference plane.

The determining the first edge point and the second edge point of the target weld on the search straight line according to the height differences between the plurality of pixel points discretized on the search straight line and the preset reference plane may include:

for each of the plurality of pixel points discretized on the search straight line, acquiring a height difference between the pixel point and the preset reference plane;

acquiring a pixel point having a maximum height difference from the preset reference plane from the plurality of pixel points discretized on the search straight line to serve as a peak point;

selecting a pixel point which is located in a first orientation of the peak point, has a distance from the peak point that meets a preset distance requirement, and has a minimum height difference from the preset reference plane from the plurality of pixel points discretized on the search straight line to serve as a first auxiliary point; and selecting a sub-pixel point having a minimum height difference from the preset reference plane from a second auxiliary point and a third auxiliary point to serve as a first edge point, where the second auxiliary point is a pixel point adjacent to the first auxiliary point and located in a first orientation of the first auxiliary point; the third auxiliary point is a pixel point adjacent to the first auxiliary point and located in a second orientation of the first auxiliary point; and the second orientation and the first orientation are symmetrical about the peak point; and selecting a pixel point which is located in a second orientation of the peak point, has a height difference from the preset reference plane within a preset height value range, and has a distance from the peak point that is closest to the distance between the first edge point and the peak point, from the plurality of pixel points discretized on the search straight line to serve as a fourth auxiliary point; and selecting a sub-pixel point having a minimum height difference from the preset reference plane from a fifth auxiliary point and a sixth auxiliary point to serve as a second edge point, where the fifth auxiliary point is a pixel point adjacent to the fourth auxiliary point and located in a first orientation of the fourth auxiliary point; and the sixth auxiliary point is a pixel point adjacent to the fourth auxiliary point and located in a second orientation of the fourth auxiliary point.

For the description of the edge point determination subunit, please specifically refer to the detailed description of step S222 in the related embodiment of the above weld quality inspection method, that is, step S222 may be executed by the edge point determination subunit.

The first edge line determination subunit is configured to fit the first edge points on the plurality of search straight lines to obtain a first edge line of the target weld.

For the description of the first edge line determination subunit, please specifically refer to the detailed description of step S223 in the related embodiment of the above weld quality inspection method, that is, step S223 may be executed by the first edge line determination subunit.

The second edge line determination subunit is configured to fit the second edge points on the plurality of search straight lines to obtain a second edge line of the target weld.

For the description of the second edge line determination subunit, please specifically refer to the detailed description of step S224 in the related embodiment of the above weld quality inspection method, that is, step S224 may be executed by the second edge line determination subunit.

In the embodiments of the disclosure, the image analysis module 330 may include a window setting unit, a first parameter acquisition unit and a second parameter acquisition unit.

The window setting unit is configured to set a plurality of scanning windows in the weld region in a second direction to divide the weld region into a plurality of sub-region images, where the second direction is a length direction of the weld region.

For the description of the window setting unit, please specifically refer to the detailed description of step S310 in the related embodiment of the above weld quality inspection method, that is, step S310 may be executed by the window setting unit.

The first parameter acquisition is configured to, for each of the plurality of sub-region images, obtain a volume parameter of a sub-target weld characterized by the sub-region image to obtain a plurality of volume parameters.

The obtaining the volume parameter of the sub-target weld characterized by the sub-region image may include:
calculating the volume parameter of the sub-target weld characterized by the sub-region image by means of double integral according to the height difference between each pixel point in the sub-region image and the preset reference plane.

For the description of the first parameter acquisition unit, please specifically refer to the detailed description of step S320 in the related embodiment of the above weld quality inspection method, that is, step S320 may be executed by the first parameter acquisition unit.

The second parameter acquisition unit is configured to take a volume parameter with a minimum value from the plurality of volume parameters as the feature parameter of the target weld.

For the description of the second parameter acquisition unit, please specifically refer to the detailed description of step S330 in the related embodiment of the above weld quality inspection method, that is, step S330 may be executed by the second parameter acquisition unit.

In addition, an embodiment of the disclosure further provides a computer readable storage medium storing a computer program which, when being executed, implements the weld quality inspection method provided by the above embodiment. For details, please refer to the above method embodiment, which will not be repeated in the embodiments of the disclosure.

To sum up, in the weld quality inspection method, apparatus and system and the electronic device provided by the embodiments of the disclosure, point cloud data of a target weldment is acquired and converted into a height map; a weld region for characterizing a target weld is determined from the height map; the weld region is analyzed to obtain a feature parameter of the target weld; and a quality inspection result of the target weld is obtained according to the feature parameter, where the target weldment includes a base material, a welding part and a target weld formed by welding the welding part to the base material. Compared with a solution of adopting a manual inspection method to inspect the weld quality in the prior art, the weld quality inspection method, apparatus and system and the electronic device provided by the embodiments of the disclosure can improve the accuracy of the quality inspection result by obtaining the quality inspection result of the target weld based on the machine vision technology and thus avoiding manual participation. For example, the weld quality inspection method provided by the embodiments of the disclosure can be applied to weld quality inspection of peripheral welding to inspect a defect of a weld with an area greater than 0.5 $mm^2$ and a depth greater than 0.2 mm, and has a strong practical application value.

In several embodiments of the disclosure, it should be understood that the disclosed weld quality inspection method and apparatus may further be implemented in other ways, while the embodiments of the above weld quality inspection apparatus are only illustrative. For example, the flowcharts and the block diagrams in the drawings show the system architectures, functions and operations which may be possibly implemented by the apparatus, the method and the computer program product according to a plurality of embodiments of the disclosure. In this regard, each block in the flowchart or the block diagram may represent a module, a program segment or a part of a code, and the module, the program segment or the part of the code contains one or more executable instructions for implementing the specified logical functions. In addition, in some alternative implementations, the functions denoted in the blocks may further occur in a different order from those denoted in the drawings. For example, two consecutive blocks may be executed in parallel in fact, and may be executed in a reverse order sometimes, depending on the functions involved. It will also be noted that each block in the block diagram and/or the flowchart, and combinations of blocks in the block diagram and/or the flowchart, may be implemented by special purpose hardware-based systems that perform the specified functions or acts, or combinations of special purpose hardware and computer instructions. In addition, in each embodiment of the present disclosure, various functional modules may be integrated to form an independent portion, or each module may exist independently, or multiple modules may be integrated to form an independent portion.

In addition, if the functions are implemented in the form of software function modules and sold or utilized as independent products, they may be stored in a computer readable storage medium. Based on this understanding, the technical solutions of the embodiments of the disclosure essentially or the part that contributes to the prior art or a part of the technical solutions may be embodied in the form of a software product. The computer software product is stored in a storage medium and includes several instructions for instructing a computer device (which may be a personal computer, a server, a network device and the like) to perform all or part of the steps of the method described in each embodiment of the disclosure. The above storage medium includes: a USB flash disk, a mobile hard disk, ROM, RAM, a magnetic disc, a compact disc or other mediums that may store program codes.

It should also be noted that relationship terms such as "first", "second", "third" and the like in the disclosure are just used for differentiating one entity or operation from the other entity or operation, and do not necessarily require or imply any practical relationship or sequence between the entities or operations. Moreover, terms of "comprise", "include" or any other variants are intended to cover non-exclusive inclusion, so that a process, a method, an article or a device which includes a series of elements not only includes such elements, but also includes other elements not listed clearly or also includes inherent elements in the process, the method, the article or the device.

The invention claimed is:

1. A weld quality inspection system, comprising an operation control component, a controller, a data collector, and an electronic device comprising a processor and a memory storing a computer program, wherein the processor is configured to execute the computer program, wherein the controller is connected with the operation control component and the data collector, and the data collector is further connected with the electronic device;
   the operation control component is configured to carry a target weldment and operate;
   the controller is configured to control the data collector to collect point cloud data of the target weldment in response to the operation control component carrying the target weldment and operating to a target position;
   the data collector is configured to send the point cloud data to the electronic device; and
   the electronic device is configured to:
      acquire the point cloud data of the target weldment,
      convert the point cloud data into a height map,
      determine a weld region for characterizing a target weld from the height map,
      analyze the weld region to obtain a feature parameter of the target weld by:
         setting a plurality of scanning windows in the weld region, in a length direction of the weld region, to divide the weld region into a plurality of sub-region images;
         for each of the plurality of sub-region images, obtaining a volume parameter of a sub-target weld characterized by each sub-region image to obtain a plurality of volume parameters; and
         taking a volume parameter with a minimum value from the plurality of volume parameters as the feature parameter of the target weld, and
      obtain a quality inspection result of the target weld according to the feature parameter,
   wherein the target weldment comprises a base material, a welding part and the target weld formed by welding the welding part to the base material.

2. The weld quality inspection system of claim 1, wherein before determining a weld region for characterizing a target weld from the height map, the electronic device is further configured to:
   preprocess the height map, where preprocessing the height map includes filtering processing and rectification processing.

3. The weld quality inspection system of claim 2, wherein the preprocessing of the height map includes:
   performing edge inspection on the height map to determine an edge straight line on a welding side of the target weldment;
   acquiring an included angle between the edge straight line and a preset reference line;
   acquiring a reference point, and obtaining a rotation matrix by taking the reference point as a rotation center and the included angle as a rotation angle; and
   based on the rotation matrix, performing affine transformation on the height map to realize the rectification processing on the height map.

4. The weld quality inspection system of claim 1, wherein determining a weld region for characterizing a target weld from the height map includes:
   selecting a first region of interest from the height map;
   determining a first edge line and a second edge line of the target weld according to height differences between a plurality of pixel points in the first region of interest and a preset reference plane; and
   taking a region image between the first edge line and the second edge line as the weld region for characterizing the target weld.

5. The weld quality inspection system of claim 4, wherein determining a first edge line and a second edge line of the target weld according to height differences between a plurality of pixel points in the first region of interest and a preset reference plane includes:
   drawing a plurality of search straight lines in the first region of interest in a first direction, where the search straight lines are perpendicular to the first direction, and the first direction is a length direction of the first region of interest;
   for each of the plurality of search straight lines, determining a first edge point and a second edge point of the target weld on the search straight line according to height differences between a plurality of pixel points discretized on the search straight line and the preset reference plane;
   fitting the first edge points on the plurality of search straight lines to obtain the first edge line of the target weld; and
   fitting the second edge points on the plurality of search straight lines to obtain the second edge line of the target weld.

6. The weld quality inspection system of claim 5, wherein for each of the plurality of search straight lines, determining a first edge point and a second edge point of the target weld on the search straight line according to height differences between a plurality of pixel points discretized on the search straight line and the preset reference plane includes:

for each of the plurality of pixel points discretized on the search straight line, acquiring a height difference between the pixel point and the preset reference plane;

acquiring a pixel point having a maximum height difference from the preset reference plane from the plurality of pixel points discretized on the search straight line to serve as a peak point;

selecting a pixel point which is located in a first orientation of the peak point, has a distance from the peak point that meets a preset distance requirement, and has a minimum height difference from the preset reference plane from the plurality of pixel points discretized on the search straight line to serve as a first auxiliary point, and selecting a sub-pixel point having a minimum height difference from the preset reference plane from a second auxiliary point and a third auxiliary point to serve as the first edge point, where the second auxiliary point is a pixel point adjacent to the first auxiliary point and located in a first orientation of the first auxiliary point; the third auxiliary point is a pixel point adjacent to the first auxiliary point and located in a second orientation of the first auxiliary point; and the second orientation and the first orientation are symmetrical about the peak point; and selecting a pixel point which is located in a second orientation of the peak point, has a height difference from the preset reference plane within a preset height value range, and has a distance from the peak point that is closest to the distance between the first edge point and the peak point, from the plurality of pixel points discretized on the search straight line to serve as a fourth auxiliary point, and selecting a sub-pixel point having a minimum height difference from the preset reference plane from a fifth auxiliary point and a sixth auxiliary point to serve as the second edge point, where the fifth auxiliary point is a pixel point adjacent to the fourth auxiliary point and located in a first orientation of the fourth auxiliary point, and the sixth auxiliary point is a pixel point adjacent to the fourth auxiliary point and located in a second orientation of the fourth auxiliary point.

7. The weld quality inspection system of claim 1, wherein obtaining a volume parameter of a sub-target weld characterized by each sub-region image includes:

calculating the volume parameter of the sub-target weld characterized by each sub-region image by means of double integral according to a height difference between each pixel point in the sub-region image and a preset reference plane.

8. The weld quality inspection system of claim 1, wherein obtaining a quality inspection result of the target weld according to the feature parameter includes:

judging whether the feature parameter is within a preset parameter range;

if the feature parameter is within the preset parameter range, determining that the quality inspection result of the target weld is qualified; and if the feature parameter is out of the preset parameter range, determining that the quality inspection result of the target weld is unqualified.

9. The weld quality inspection system of claim 1, wherein obtaining a quality inspection result of the target weld according to the feature parameter includes:

inputting the feature parameter into a preset classification model, and obtaining an output result of the classification model, where the output result includes a first result for characterizing that the quality inspection result of the target weld is qualified, and a second result for characterizing that the quality inspection result of the target weld is unqualified.

10. The weld quality inspection system of claim 9, wherein before inputting the feature parameter into a preset classification model, the electronic device is further configured to:

acquire a feature parameter of a standard weld included in each of a first target number of standard weldments as a standard parameter to obtain a first target number of standard parameters;

acquire a feature parameter of an unqualified weld included in each of a second target number of defective weldments as an unqualified parameter to obtain a second target number of unqualified parameters; and train an initial learning model using the first target number of standard parameters and the second target number of unqualified parameters to obtain the classification model.

* * * * *